United States Patent
Sandberg et al.

(10) Patent No.: US 6,723,318 B1
(45) Date of Patent: *Apr. 20, 2004

(54) TARGETING OF BIOMOLECULES

(75) Inventors: Bengt E. B. Sandberg, Hjarup (SE); Rune Nilsson, Lund (SE)

(73) Assignee: Mitra Medical Technology AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/689,421

(22) Filed: Oct. 12, 2000

Related U.S. Application Data

(63) Continuation-in-part of application No. 08/090,047, filed as application No. PCT/SE92/00020 on Jan. 15, 1992.

(30) Foreign Application Priority Data

Jan. 17, 1991 (SE) .............................................. 9100142

(51) Int. Cl.[7] .............................................. A61K 39/00
(52) U.S. Cl. ............................ 424/140.1; 604/4; 604/5; 604/28
(58) Field of Search ............................. 604/4; 424/94.1, 424/130.1, 140.1; 514/2, 21; 435/283, 267

(56) References Cited

U.S. PATENT DOCUMENTS

| | | |
|---|---|---|
| 4,215,688 A | 8/1980 | Terman et al. |
| 4,223,672 A | 9/1980 | Terman et al. |
| 4,350,156 A | 9/1982 | Malchesky et al. |
| 4,371,515 A | 2/1983 | Chu |
| 4,375,414 A | 3/1983 | Strahilevitz |
| 4,551,435 A | 11/1985 | Liberti et al. |
| 4,576,928 A | 3/1986 | Tani et al. |
| 4,687,808 A | 8/1987 | Jarrett et al. |
| 4,800,016 A | 1/1989 | Yang |
| 4,820,261 A | 4/1989 | Schmoll et al. |
| 4,824,432 A | 4/1989 | Skurkovich et al. |
| 4,846,786 A | 7/1989 | Freed et al. |
| 4,863,713 A | 9/1989 | Goodwin et al. |
| 4,865,841 A | 9/1989 | Balint, Jr. et al. |
| 4,877,599 A | 10/1989 | Lees |
| 4,885,207 A | 12/1989 | Johnson et al. |
| 5,069,662 A | 12/1991 | Bodden |
| 5,122,112 A | 6/1992 | Jones |
| 5,149,425 A | 9/1992 | Mazid |
| 5,252,466 A | 10/1993 | Cronan, Jr. |
| 5,474,772 A | 12/1995 | Maddock |

FOREIGN PATENT DOCUMENTS

| | | |
|---|---|---|
| EP | 0 110 409 A2 | 6/1984 |
| EP | 0 132 534 A2 | 2/1985 |
| WO | WO 88/06045 | 8/1988 |
| WO | WO 90/07929 | 7/1990 |
| WO | WO 91/01749 | 2/1991 |
| WO | WO 00/02050 | 1/2000 |

OTHER PUBLICATIONS

Wang et al. (Aug. 2000) *Cancer Biotherapy and Radiopharmaceuticals* 15:396.

Hofheinz et al., "Monoclonal Antibody", Proceedings of Am. Assoc. Cancer Research, 28:391 (1987).

Ingvar et al., "Biokinetics of Radiolabeled Monoclonal Antibodies in Heterotransplanted Nude Rats: Evaluation of corrected Specific Tissue Uptake", Journal of Nuclear Medicine, 30:1224–1234 (1989).

Johnson et al., "Radioimmunoadsorption of KC–4G3 Antibody in Peripheral Blood: Implications for Radioimmunotherapy", Antibody Immunoconjugates and Radiopharmaceuticals, 4:885–893 (1991).

Klibanov et al., "Blood Clearance of Radiolabeled Antibody: Enhancement by Lactosamination and Treatment with Biotin–Avidin or Anti–Mouse IgG Antibodies", The Journal of Nuclear Medicine, 29:1951–1956 (1988).

Lear et al., "Improved Tumor Imaging with Radiolabeled Monoclonal Antibodies by Plasma Clearance of Unbound Antibody with Anti–antibody Column", Radiology 179:509–512 (1991).

Marshall et al., "Clearance of Circulating Radio–Antibodies using Streptavidin or Second Antibodies in a Xenograft Model", Br. J. Cancer, 69:502–507 (1994).

Marshall et al., "Galactosylated Streptavidin for Improved Clearance of Biotinylatd Intact and F(ab') Fragments of an Anti–Tumor Antibody", Br. J. Cancer, 71:18–24 (1995).

Nilsson et al., "Extracorporeal Immunoadsorption Therapy on Rats. In Vivo Depletion of Specific Antibodies", Clin. Exp. Immunol., 82:440–444 (1990).

Norrgren et al., "A General, Extracorporeal Immunoadsorption Method to Increase the Tumor–to–Normal Tissue Ratio in Radioimmunoimaging and Radioimmunotherapy", The Journal of Nuclear Medicine, 34:448–454 (1993).

Norrgren et al., "Evaluation of Extracorporeal Immunoadsorption in Radioimmunoimaging and Radioimmunotherapy", Proceeds from 3rd Conferenced 4:54 (1990).

(List continued on next page.)

*Primary Examiner*—Jean C. Witz
(74) *Attorney, Agent, or Firm*—Swanson & Bratschun, LLC

(57) ABSTRACT

The present invention provide methods to improve the treatment of cancer in mammals, including ovarian cancer, where intraperitoneal administration of cytotoxic medical agents or immunoconjugates are utilized. The invention provides means of substantially reducing the level of cytotoxic medical agents or immunoconjugates in the circulating blood. Hence, the organ exposure of circulating cytotoxic agents is minimized using the invention and the invention offers opportunities to use more effective dose treatment regime.

5 Claims, 4 Drawing Sheets

OTHER PUBLICATIONS

Norrgren et al., "Contrast Enhancement in RII and Modification of the Therapeutic Ratio in RIT: A Theoretical Evaluation of Simulated Extracorporeal Immunoadsorption", Antibody Immunoconjucates & Radiopharmaceuticals, 5:61–73 (1992).

Schriber et al., "Strategies to Enhance the Localization of Anticancer Immunoconjugates", Current Medicinal Chemistry, 2:616–629 (1995).

Sharkey et al., "Development of a Streptavidin–Anti–Carcinoembryonic Antigen Antibody, Radiolabeled Biotin Pretargeting Method for Radioimmunotherapy of Colorectal Cancer, Studies in a Human Colon Cancer Xenograft Model", Bioconjugate Chem., 8:595–604 (1997).

Sinitsyn et al., "Rapid Blood Clearance of Biotinylated IgG After Infusion of Avidin" The Journal of Nuclear Medicine, 30:66–69 (1989).

Strand et al., "Plasmapheresis as a Tool for Enhancing Contrast in Radioimmunoimaging and Modifying Absorbed Doses in Radioimmunotherapy", Abstract Med. Phys., 16:465 (1989).

Wahl et al., "Systemic Perfusion: A Method of Enhancing Relative Tumor Uptake of Radiolabeled Monoclonal Antibodies", The Journal of Nuclear Medicine, 28:715 (1987).

Wahl et al., "Overview: Experimental Targeting", Proceeds from 34d Conference 4:15 (1990).

Wahl et al., "Systemic Perfusion: A Method of Enhancing Relative Tumor Uptake of Radiolabeled Monoclonal Antibodies", Nucl. Med. Biol. 15:611–616 (1988).

Ward et al., "The Treatment of Intraperitoneal Malignant Disease with Monoclonal Antibody Guided I Radiotherapy", Br. J. Cancer 58:658–662 (1988).

G. Ashwell and A.G. Morell, "The Role of Surface Carbohydrates in the Hepatic Recognition and Transport of Circulating Glycoproteins", Carbohydrates and Plasma Glycoproteins, Adv. Enzymol., 41:99–128, (1974).

DeNardo et al., " Immunoadsorption: An Enhancement Strategy for Radioimmunotherapy", The Journal of Nuclear Medicine, 34(6):1020–1027 (1993).

DeNardo et al., "Radioimmunotherapy in Patients with Metastatic Breast Cancer", The Journal of Nuclear Medicine, 33:862–863 (1992).

DeNardo et al., "Efficacy of Immunophoresis to Reduce Myelosuppression in Radioimmunotherapy", The Journal of Nuclear Medicine, 33:863 (1992).

Dienhart et al., "Extracorporeal Immunoadsorption of Radiolabeled Monoclonal Antibody: A Method for Reduction of Background Radioactivity and Its Potential Role During the Radioimmunotherapy of Cancer", Antibody Immunoconj. Radiopharm. 7:225 (1991).

Senter, P.D., "Activation of Prodrugs by Antibody–enzyme Conjugates: A New Approach to Cancer Therapy", The FASEB Journal, 4:188–193 (1990).

Ferrone et al., "Improvement by Affinity Chromatography on Antidiotypic mAb ofthe In Vitro Immunoreactivity of Radiolabeled Anti–HMW–MAA mAb TP61.5 and of its In Vivo Targeting in Nude Mice Bearing Human Melanoma Lesions", Proceeds from 3rd Conference 4:15 (1990).

Garkavij et al., "Extracorporeal Immunoadsportion from Whole Blood Based on the Avidin–Biotin Concept" Acta Oncologica 35:309–312 (1996).

Garkavij et al., "Extracorporeal Whole–Blood Immunoadsorption Enhances Radioimmunotargeting of Iodine–125–Labeled BR96–Biotin Monoclonal Antibody", The Journal of Nuclear Medicine, 38:895 (1997).

Henry et al.,"Improved Monoclonal Antibody Tumor/Background Ratios with Exchange Transfusions", Proceeds from 3rd Conference, 4:22 (1990).

Henry et al., "Improved Monoclonal Antibody Tumor/Background Ratios with Exchange Transfusions", Nucl. Med. Biol 18:565 (1991).

TARGETING OF BIOMOLECULES

RELATEDNESS OF THE APPLICATION

The subject application is a continuation-in-part of copending U.S. Ser. No. 08/090,047, filed Oct. 12, 1993, which is 35 USC §371 national phase application of PCT/SE92/00020, filed Jan. 15, 1992, which claims priority to SE 9100142-0, filed Jan. 17, 1991. These predecessor applications are incorporated herein in their entirety by reference.

FIELD OF THE INVENTION

This invention relates to a methods of improving the tumor to non-tumor ratio of cytotoxic targeting agents in the treatment of disseminated carcinomas, in particular ovarian carcinomas, by reducing the concentration of the cytotoxic medical agent in the blood circulation after intraperitoneal administration of a cytotoxic agent and thereby facilitating a higher dosage and thereby a more effective treatment regime without exposing the vital organs to higher toxicity.

Among the various methods presented in this invention, means of extracorporeal removal of the circulating toxic agents is particularly attractive.

BACKGROUND OF THE INVENTION

Ovarian cancer is the sixth most common cancer among women, excluding non-melanoma skin cancers. The American Cancer Society estimates that about 23,100 new cases of ovarian cancer will be diagnosed in the United States during 2000. Ovarian cancer accounts for 4% of all cancers in women.

Ovarian cancer is also the fifth most common cause of cancer deaths among women, causing more deaths than any other cancer of the female reproductive system. It is estimated that there will be about 14,000 deaths from ovarian cancer in the United States during 2000. About 78% of ovarian cancer patients survive one year after diagnosis and over 50% survive longer than five years after diagnosis. If diagnosed, and treated while the cancer has not spread outside the ovary, the five-year survival rate is 95%. However, only 25% of all ovarian cancers are found at this early stage.

The 5-year survival rate refers to the percent of patients who survive at least 5 years after their cancer is diagnosed. Five-year relative survival rates exclude from the calculations patients dying of other diseases, and are considered to be a more accurate way to describe the prognosis for patients with a particular type and stage of cancer. Of course, 5-year survival rates are based on patients diagnosed and initially treated more than 5 years ago. Improvements in treatment often result in a more favorable outlook for recently diagnosed patients.

There are many types of tumors that can start growing in the ovaries. Some are benign (non-cancerous) and never spread beyond the ovary. These patients can be cured by surgically removing one ovary or the part of an ovary containing the tumor. Other types of ovarian tumors are malignant (cancerous) and may spread to other parts of the body.

In general, ovarian tumors are named according to the kind of cells the tumor started from and whether the tumor is benign or cancerous. There are three main types of ovarian tumors. Epithelial tumors start from the cells that cover the outer surface of the ovary. Cancerous epithelial tumors are called carcinomas. Germ cell tumors start from the cells that produce the eggs (ova). Stromal tumors start from connective tissue cells that hold the ovary together and produce the female hormones, oestrogen and progesterone.

Epithelial ovarian carcinomas (EOC) accounts for 85%–90% of ovarian cancers. The cells of EOC may have several forms that can be recognized under the microscope. In addition to their classification by cell type, EOCs are also given a grade and a stage. The grade is on a scale of 1, 2, or 3. Grade 1 EOC more closely resembles normal tissue and tends to have a better prognosis. Grade 3 EOC less closely resembles normal tissues and usually has a worse outlook. The tumor stage describes how far the tumor has spread from where it started in the ovary.

Effective therapeutic methods for the treatment of ovarian cancer have been subjected to intensive research. Most women suffering from ovarian carcinomas die of loco-regional recurrence and peritoneal dissemination; hence, regional therapy has been the main focus for some time. Experience with intraperitoneal therapy of this tumor using conventional chemotherapy agents (Howel S. et. al. Intraperitoneal cisplatinum-based chemotherapy for ovarian carcinoma, *Semin. Oncol.* 1991,18 (Suppl 3), 5–10); radioactive colloids (Rosenhein N. B. et. al. Radiocolloids in the treatment of ovarian cancer, *Obstet Gynecol Surv* 1997, 34, 708–20); immunoadjuvants (Bast R. C. et. al. Intraperitoneal immunotherapy of human ovarian carcinoma with corynebacterium parvum. *Cancer Res.* 1983, 43, 1395–1401); cytokines (Navoli M. et. al. Intraperitoneal recombinant alpha-2-interferon alternating with cisplatin as salvage therapy for minimal residual-disease ovarian cancer: a phase II study. *J. Clin. Oncol* 1990, 8(6), 1036–1041) have been reported.

Another area of investigation involves treatment with very high doses of anticancer drugs, and then "rescuing" the woman from the side effects with infusions of her own bone marrow stem cells or peripheral blood stems cells (immature blood cells that may be taken from the bone marrow or removed from the bloodstream by using a special filtering process). The bone marrow or peripheral blood stem cells are removed before a high dose of chemotherapy is administered and is returned to the woman (reinfused) after the high-dose treatment is complete. In that way, the side effect of suppressed blood cell production is overcome. This is an extremely high-risk, experimental procedure because, for the time, the woman is without her normal supply of blood cells and is very vulnerable to infection.

Targeting biomolecules such as tumor specific monoclonal antibodies are widely used in the treatment of haematological cancer diseases and more recently in the treatment of disseminated solid tumors (Breitz H. B. et. al. Radioimmunotherapy of Solid Tumours, in *Radioimmunotherapy of Cancer*, eds. P. G. Abrams & A. R. Fritzberg, Marcel Dekker, Inc., New York, 2000, p.265–306).

A number of tumor specific monoclonal antibodies and immunoconjugates, suitable for in vivo diagnosis and treatment of ovarian cancer, have been described in U.S. Pat. No. 4,958,009 (Anti-human ovarian cancer immunotoxins and methods of use thereof), in U.S. Pat. No. 5,817,313 (Monoclonal antibodies and conjugates thereof useful for the treatment of cancer), in U.S. Pat. No. 5,804,187 (Modified antibodies with human milk fat globule specificity) and in U.S. Pat. No. 5,650,291 (Monoclonal antibodies against an antigen associated with ovarian cervical and other tumors).

Over the past decade a number of clinical studies using intraperitoneal (i.p.) radioimmunotherapy in ovarian cancer have been reported. Various types of monoclonal antibodies including HMFG-1, HMFG-2, AUA-1 and H 17E2 have been labelled with I-131, Y-90 and Re-186, and injected into the peritoneal cavity through peritoneal dialysis catheter under local anaesthesia in volumes ranging from 1–2 liter of normal saline and a specific activity of 4–8 mCi/mg antibody.

The effective dose for i.p. I-131 labelled antibodies is thought to be 150 mCi and the mean peak radioactivity in serum is at 44 hrs, corresponding to 26% of the total injected dose. Most of the radioactivity given (80%) is found as free iodine in the urine. However, when Y-90 labelled antibodies are used, the mean peak of radioactivity in serum is 23%, and only 8–11% of the injected dose is released in the urine after 72 hrs (Rosenblum M. G. et. al. Clinical pharmacology, metabolism and tissue distribution of Y-90-labelled monoclonal antibody B27.3 after intraperitoneal administration. *J. Natl. Cancer Inst.* 1991 (83) 1629).

Although, toxic exposure to the peritoneum and its close surrounding is usually well tolerated and is 4-70-fold more advantageous than the i.v. route for targeting of peritoneal tumor sites (Ward, B. G. et. al. Localization of radio iodine conjugated to the monoclonal antibody HMFG-2 in human ovarian carcinoma: assessment of intravenous and intraperitoneal routes of administration. *Cancer Res.* 1987 (47) 4719; Ward B. G. et. al. Radiolabelled monoclonal antibodies in oncology. III Radioimmunotherapy. *Nucl. Med. Commun.* 1991 (12) 333), a high percentage of the injected activity still localizes in normal tissues; the dose-limiting organ being the bone marrow. Myelosuppression arises 4–6 weeks after the initial injection. Grade 3 platelet and granulocyte toxicity (according to the WHO standard) was observed at a total dose of 20 mCi with Y-90 labelled antibody and 160 mCi with I-131 (Stewart J. S. et. al. Intraperitoneal I-131 and Y-90 labelled monoclonal antibodies for ovarian cancer: pharmacokinetics and normal tissue dosiometry. *Int. J. Cancer* 1988 (3 suppl.), 71; Stewart J. S. et. al. Intraperitoneal yttrium-90 labelled monoclonal antibody in ovarian cancer. *J. Clin. Oncol.* 1990, (8), 1941; Maraveyas A. et. al. Pharmacokinetics and toxicity of an yttrium-90-CITC-DTPA-HMFG-1 radioimmunoconjugate for intraperitoneal radioimmunotherapy of ovarian cancer. *Cancer* 1993 (73) 1067), while grade 3 and 4 haematological toxicity was observed at a total dose of 150 mCi with Re-186 (Jacobs A. J. et. al. A phase I trial of a rhenium 186-labeled monoclonal antibody administered intraperitoneally in ovarian cancer carcinoma: toxicity and clinical response. *Obstet. Gynecol.* 1993 (82) 586).

From the review of the relevant clinical trials, it is clear that i.p. radioimmunotherapy is of benefit mainly to patients with small-volume disease. All studies performed agree that patients with lesions <2 cm have a prolonged disease-free period when compared with historical control group (Hird et. al. Adjuvant therapy of ovarian cancer with radioactive monoclonal antibody. *Br. J. Cancer* 1993 (82) 586). In the same group of patients, tumor regression has been reported for a number of cases (Epenetos A. A. et. al. Antibody guided irradiation of malignant lesions: three cases illustrating a new method of treatment. *Lancet* 1984, 1441; Maraveyas A. et. al. Pharmacokinetics and toxicity of an yttrium-90-CITC-DTPA-HMFG-1 radioimmunoconjugate for intraperitoneal radioimmunotherapy of ovarian cancer. *Cancer* 1993 (73) 1067) as well as decrease in tumor size (Jacobs A. J. et. al. A phase I trial of a rhenium 186-labeled monoclonal antibody administered intraperitoneally in ovarian cancer carcinoma: toxicity and clinical response. *Obstet. Gynecol.* 1993 (82) 586).

However, the results are rather poor in patients with nodules >2 cm in diameter subjected to radioactive doses at, or close to, the maximum tolerated dose, since too little of the radioactive antibodies are penetrating the tumorous tissue and the high-energy radiation reaches the limit of its distant killing effect (Ward B. et. al. The treatment of intraperitoneal malignant disease with monoclonal antibody guided 131-I radiotherapy. *Br. J. Cancer* 1988 (58) 658). This group of patients number more than 50% of patients in need of treatment. Thus, the dose necessary to reach an effective therapy in this group of patients is hampered by the accumulation of radioactivity in the blood circulation, leading to toxicity of normal organs, notably the bone marrow.

Other carcinomas where intraperitoneal administration of cytotoxic medical agent could be applicable, either alone, or in combination with intravenous administration, includes, but is not limited to, colon and/or rectal cancer.

Most medical agents, and in particular larger molecules, administered into the peritoneal cavity are transported to the blood mainly through the lymphatic system, provided that the peritoneum remains intact. If these molecules are toxic to cells they may do considerable damage to body tissues outside the peritoneal cavity such as kidney, liver, lung and bone marrow, and may even be fatal. It is desirable to remove such materials from the blood as quickly as possible. Although the body has natural clearance mechanisms to remove exogenous molecules from the blood circulation, these systems are rather slow for in particular immunoglobulins; leading to a high toxic exposure to the clearing organs such as liver and/or kidney.

Various means to clear the blood from cytotoxic targeting biomolecules (e.g. therapeutic or diagnostic monoclonal antibodies) after i.v. administration have been reported (see review article by Schriber, G. J. & Kerr, D. E., *Current Medical Chemistry*, 1995, Vol. 2, pp 616–629).

In the so-called avidin chase modality, avidin or streptavidin is administered systemically after administration of the therapeutic or diagnostic antibody to which biotin has been attached, at a time when a sufficient amount of the antibody has been accumulated in the tumor. Avidin or streptavidin will associate with the antibodies and the so formed immunocomplex will clear from the blood circulation via the reticuloendothelial system (RES) and be cleared from the patient via the liver. These procedures will improve the clearance of biotinylated cytotoxic antibodies. An alternative approach to the same end, is the use of anti-idiotypic antibodies. However, all these methods rely on the liver or kidney for blood clearance and thereby expose either or both of these vital organs as well as the urinary bladder to high dose of cytotoxicity. Another major drawback of the methods is the immunogenicity of these agents, particularly the streptavidin, which prevent repetitive treatments once the immune response has been developed.

Extracorporeal techniques for blood clearance are widely used in kidney dialysis, where toxic materials build up in the blood due to a lack of kidney function. Other medical applications where an extracorporeal device can be used include: removal of radioactive materials; removal of toxic levels of metals; removal of toxins produced from bacteria or viruses; removal of toxic levels of drugs, and removal of whole cells (e.g. cancerous cells, specific haematopoietic cells—e.g. B, T, or NK cells) or removal of bacteria and viruses.

In a preferred embodiment of the invention, a cytotoxic targeting biomolecule (e.g. immunoconjugate) used for therapy of human ovarian cancer is removed from the blood to improve its ratio of target-to-non-target concentration. An improved target-to-non-target ratio provides a better therapeutic index. Specific tissue or organ localization of a biomolecule is a very important factor in its effective application. Lack of specific tissue localization is of particular importance in the treatment with cytotoxic biomolecules, where the desired effect is to kill certain types of cells such as in the treatment of cancer. In order to enhance the specificity, tumor specific monoclonal antibodies are used as a carrier (immunoconjugates) of various cytotoxic moieties, such as, but not limited to, radionuclides, chemotherapy drugs, synthetic or naturally occurring toxins, immunosuppressive agents, immunostimulating agents, and enzymes used in prodrug protocols (Meyer et al., *Bioconjugate Chem.* 6, 440–446; 1995; Houba et al., *Bioconjugate Chem.* 7, 606–611, 1996; Blakey et al., *Cancer Res.* 56, 3287–3292, 1996).

Although tumor-specific immunoconjugates are selectively bound to tumor cells, an initial high concentration of the cell-toxic immunoconjugate in the peritoneal fluid is necessary to reach a sufficiently high concentration in the target tissue. While required for optimal therapy of the cancer, the high concentration of cytotoxic material in the peritoneal fluid will gradually increase the level of the cell toxic material in the blood and other non-tumor tissues, in most cases leading to tissue damage and/or lesion formation in sensitive and vital tissues like the bone marrow. Although, bone marrow rescue is sometimes used to circumvent these potentially lethal effects, such rescue is both extremely costly and poses high risk for the patient.

Even in cases where the bone marrow rescue is effective, other sensitive organs like the liver, kidney, spleen, lung, etc. can be irreparably damaged. The most effective method for preventing tissue and bone marrow damage from toxic materials in blood is to dramatically decrease the amount of that toxic material in the blood. Of course, this must be accomplished in a manner that retains the therapeutic level of toxic material in the tissue being treated (e.g. tumor). Direct transport from the peritoneal fluid to the blood circulation is not considered to be of major significance for most cytotoxic medical agents compared to the lymphatic transportation route. Hence, the concentration of cytotoxic medical agents in the peritoneal fluid is only to a small extent dependent on the concentration of the same medical agent the blood circulation.

Various methods have been proposed to rapidly clear radiolabeled antibodies from blood circulation after the tumor has accumulated a sufficient quantity of immunoconjugate to obtain a diagnosis or therapy. Some of the methods employed involve enhancement of the body's own clearing mechanism through the formation of immune complexes. Enhanced blood clearance of radiolabeled antibodies can be obtained by using molecules that bind to the therapeutic antibody, such as other monoclonal antibodies directed towards the therapeutic antibody (Klibanov et. al., *J. Nucl. Med.* 29, 1951–1956, 19888; Marshall et al. *Br. J. Cancer* 69, 502–507, 1994; Sharkey et al. *Bioconjugate Chem.* 8, 595–604, 1997), avidin/streptavidin (Sinitsyn et al., *J. Nucl. Med.* 30, 66–69,1989; Marshall et. al., *Br. J. Cancer*, 71, 18–24, 1995), or glycosyl containing compounds which are removed by receptors on liver cells (Ashwell and Morell, *Adv. Enzymol.* 41, 99–128, 1974). Still other methods involve removing the circulating immunoconjugates through extracorporeal methods (see review article by Schriber, G. J. & Kerr, D. E., *Current Medical Chemistry*, 1995, Vol. 2, pp 616–629).

The extracorporeal techniques used to clear a medical agent from blood circulation are particularly attractive because the toxic material is rapidly removed from the body. Application of these methods in the context of immunotherapy have been previously described (Henry Chemical Abstract, 1991, Vol.18, pp. 565; Hofheinze D et al., *Proc. Am. Assoc. Cancer. Res.* 1987 Vol. 28, pp 391; Lear J K, et al. Radiology 1991, Vol. 179, pp. 509–512; Johnson T. K. et. al. *Antibody Immunoconj. Radiopharm.* 1991, Vol. 4, pp. 509; Dienhart D. G., et al. *Antibody Immunoconj. Radiopharm.* 1991, Vol. 7, pp. 225; DeNardo G. L. et al. *J. Nucl. Med.* 1993, Vol. 34, pp1020–1027; DeNardo S. J. et. al. *J. Nucl. Med.* 1992, Vol. 33, pp. 862–863; DeNardo G. L. *J. Nucl. Med.* 1992, Vol. 33, pp. 863–864; and U.S. Pat. No. 5,474, 772 (Method of treatment with medical agents.).

To make the blood clearance more efficient and to enable processing of whole blood, rather than blood plasma as the above methods refer to, the medical agents (e.g. tumor specific monoclonal antibody carrying cell killing agents or radionuclides for tumor localization) have been biotinylated and cleared by an avidin-based adsorbent on a column matrix. A number of publications provide data showing that this technique is both efficient and practical for the clearance of biotinylated and radionuclide labelled tumor specific antibodies (Norrgren K, et. al. *Antibody Immunoconj. Radiopharm.* 1991, Vol. 4, pp 54; Norrgren K, et .al. *J. Nucl. Med.* 1993, Vol. 34, pp. 448–454; Garkavij M, et. al. *Acta Oncologica* 1996, Vol. 53, pp.309–312; Garkavij M, et. al. *J. Nucl Med.* 1997, Vol.38, pp.895–901. These techniques are also described in EP0 567 514 (A method and a system for enhanced in vivo clearance of diagnostic and/or therapeutic agents by extracorporeal depletion, and the use of said agents for said purpose). A further development of this method where simultaneous labelling of biotin and radionuclides is described in a patent application by Nilson et al., PCT/SE92/0020 (from which priority is claimed), A Method and a System for Enhanced In Vivo Clearance of Diagnostic and/or Therapeutic Agents by Extracorporeal Depletion, and the Use of said Agents for Said Purpose; and an application by S. Wilbur & B. E. B. Sandberg PCT/SE98/01345, Trifunctional reagent for the conjugation to a biomolecule.

Apart from the prolonged circulation time leading to undesired exposure of toxic immunoconjugate to healthy tissue, inadequate tumor tissue penetration and non-specific organ retention and metabolism contribute to a low therapeutic index ratio. Due to these problems, multi-step antibody-based radionuclide delivery approaches have been extensively investigated. The basic concept involves first the injection of a lesion-specific targeting moiety, which apart from binding specifically to the lesion also has the feature of binding to a subsequently injected radioactive diagnostic agent or a therapeutic agent. By separating these two events one can allow the slow tissue penetrating non-radioactive/ non-cytotoxic antibody sufficient time to accumulate in the tumor mass, while the agent carrying the radionuclide/ cytotoxin could be selected for more rapid tissue penetration. However, a prerequisite is that the former (and preferably also the later) can be cleared rapidly from the blood circulation.

The so called two and three-step approaches have recently been reviewed in the context of intraperitoneal administration in ovarian cancer therapy (Syrigos K. N. & Epenetos A. A. (2000) Intraperitoneal Radioimmunotherapy of Ovarian Cancer in *Radioimmunotherapy of Cancer*, eds. P. G. Abrams & A. R. Fritzberg, Marcel Dekker, Inc., New York, p. 315–316).

SUMMARY OF THE INVENTION

The present invention relates to improvements in the diagnosis and treatment of peritoneal cancers, including ovarian cancer. The method is based on reducing the level of cytotoxic medical agents or toxic immunoconjugates from the blood circulation, after intraperitoneal injection of these compounds. By depleting the circulating cytotoxic medical agent or immunoconjugate, it is possible both to decrease the toxic side effect on other organs and at the same time increase the therapeutic dose in a single administration or through administration of multiple doses, which results in an increased penetration of the tumor tissue by the cytotoxic medical agent or immunoconjugate.

Thus, in one embodiment, the subject invention comprises a method for improving the treatment of intraperitoneal cancers in mammals comprising: (a) administering a biomolecule intraperitoneally to said mammal; and (b) substantially reducing the level of said biomolecule or a cytotoxic fragment thereof in the blood circulation at suitable time intervals, whereby side effects associated with circulating biomolecule or cytotoxic fragment are reduced. Preferably, the reduction of biomolecule or cytotoxic fragment in the circulation is achieved by passing the blood or a component thereof through an extracorporeal adsorption device. The blood component may be serum or plasma. The extracorporeal device comprises a solid support with a receptor bound thereto; and the biomolecule or cytotoxic fragment is conjugated to an affinity ligand with a high affinity to the receptor. Alternatively, the biomolecule or cytotoxic fragment has a high affinity to the receptor.

The biomolecule can be a cytotoxic medical agent; a cytotoxic medical agent conjugated to a targeting agent; and a targeting agent conjugated to a cytotoxic moiety which is selected from the group consisting of a radionuclide, a chemotherapy drug, a synthetic or naturally occurring toxin, an immunosuppressive, an immunostimulant, and a prodrug activating enzyme. If the biomolecule is the cytotoxic medical agent conjugated to a targeting agent, it is preferred that the affinity ligand be directly covalently bound to the cytotoxic medical agent. If the biomolecule is the targeting agent conjugated to the cytotoxic moiety, it is preferred that the affinity ligand be directly covalently or coordinately bound to the radionuclide or directly covalently bound to the chemotherapy drug, the synthetic or naturally occurring toxin, the immunosuppressive, the immunostimulant, or the prodrug activating enzyme.

The cytotoxic fragment of the biomolecule is a molecule comprising a radionuclide or a toxic metabolite or structure derived from the cytotoxic medical agent, the chemotherapy drug, the synthetic or naturally occurring toxin, the immunosuppressant, the immunostimulant or the prodrug activating enzyme.

In a preferred embodiment, the invention comprises a method for improving the treatment of intraperitoneal cancers in mammals comprising: (a) administering a conjugate of a biomolecule and an affinity ligand intraperitoneally to the mammal; and (b) substantially reducing the level of said biomolecule or cytotoxic fragment thereof in the blood circulation by passing at suitable time intervals the blood or a component thereof through an extracorporeal device comprising a solid support having a receptor bound thereto, the affinity ligand having a high affinity to the receptor, whereby the level of biomolecule or cytotoxic fragment in the circulation is reduced.

The invention also comprises a system for substantially reducing the level of a biomolecule or cytotoxic fragment thereof in a mammal's blood or component thereof, wherein the biomolecule has been administered intraperitoneally, said system comprising an extracorporeal device having immobilized receptors therein, through which the mammal's blood or a component thereof is passed, whereby the receptors, which have a high affinity for the biomolecule or the cytotoxic fragment, or for an affinity ligand bound to the biomolecule or the cytotoxic fragment, immobilize the biomolecule or the cytotoxic fragment in the device; means for transporting the blood or blood component to the extracorporeal device; and means for delivering treated blood or blood component from the extracorporeal device to the mammal.

The subject invention further comprises a method for improving the imaging of peritoneal cancers in mammals comprising: (a) administering a conjugate of a radionuclide and a targeting agent intraperitoneally to said mammal, wherein said targeting agent has a high affinity for the cancer; and (b) substantially reducing the level of radionuclide in the blood circulation at suitable time intervals, whereby side effects associated with circulating radionuclide are reduced or whereby imaging contrast is improved. Preferably, the reduction of radionuclide in the circulation is achieved by passing the blood or a component thereof through an extracorporeal adsorption device. The extracorporeal device comprises a solid support with a receptor bound thereto, and the conjugate of radionuclide and targeting agent, or a cytotoxic fragment thereof, is further conjugated to an affinity ligand with a high affinity to the receptor. Alternatively, the receptors in the extracorporeal may have a high affinity to the targeting agent. In a preferred embodiment, a radionuclide is directly covalently or coordinately bound to the affinity ligand, which is directly covalently bound to the targeting agent.

The invention can be illustrated with the simulation exemplified in Example 1. As is explained in Example 1, clinical data from Maraveyas, A. et al. (Cancer 73:1067–1075, 1994) relating to intraperitoneal administration of $^{90}$Y-HMFG-1 to patients with ovarian cancer were utilized in the simulation. These data were utilized to simulate the effects of two extracorporeal adsorptions with Mitradep® (a blood filter having avidin immobilized to agarose particles) conducted at various time after administration of the antibody conjugate. Each adsorption is assumed to remove 90 per cent of the circulating conjugate. It is also assumed that the rate of transport of conjugate from the intraperitoneal volume to blood or the biological half-life of the conjugate in blood is not influenced by the extracorporeal adsorptions. The results illustrated in FIG. 1 illustrate how treatment of the blood at selected time intervals after administration can significantly or substantially reduce the level of biomolecule in the blood, thereby substantially reducing side effects associated with the circulating biomolecule and enhancing the target to non-target ratio for the biomolecule. This improved ratio can result in decreased side effects and/or improved contrast for imaging.

Although the present invention is described for application to human ovarian carcinoma it is also applicable to other types of human cancer diseases where intraperitoneal administration is deemed preferable. The subject procedure is also suitable for the treatment of other mammalian species. The clearance of the biomolecule from the blood is achieved by passing the patient's whole blood through a device that specifically adsorbs the biomolecule. In the most preferred application, the biomolecule is labelled with biotin and the blood clearance is achieved by passing the blood on-line through a device coated with avidin or streptavidin. Such a device is described in EP0 567514 and exhibits the proper characteristics of the matrix and means of immobilizing the biotin-binding entity for processing of whole blood and obtaining excellent clearance in a reasonable time period. The biocompatibility of an agarose matrix containing immobilized avidin for clinical use has been reported (Bosch, T. et al., Ex Vivo Biocompatibility of Avidin-Agarose: A New Device for Direct Adsorption of Biotinylated Antibodies from Human Whole Blood. *Artificial Organs*, 2000). It should be stressed that all extracorporeal applications where the patient's whole blood is processed would also be applicable for the processing of human plasma, although such a system would be both more cumbersome and less efficient.

All references cited herein are incorporated by reference in their entireties.

DETAILED DESCRIPTION OF THE INVENTION

Figure 1:
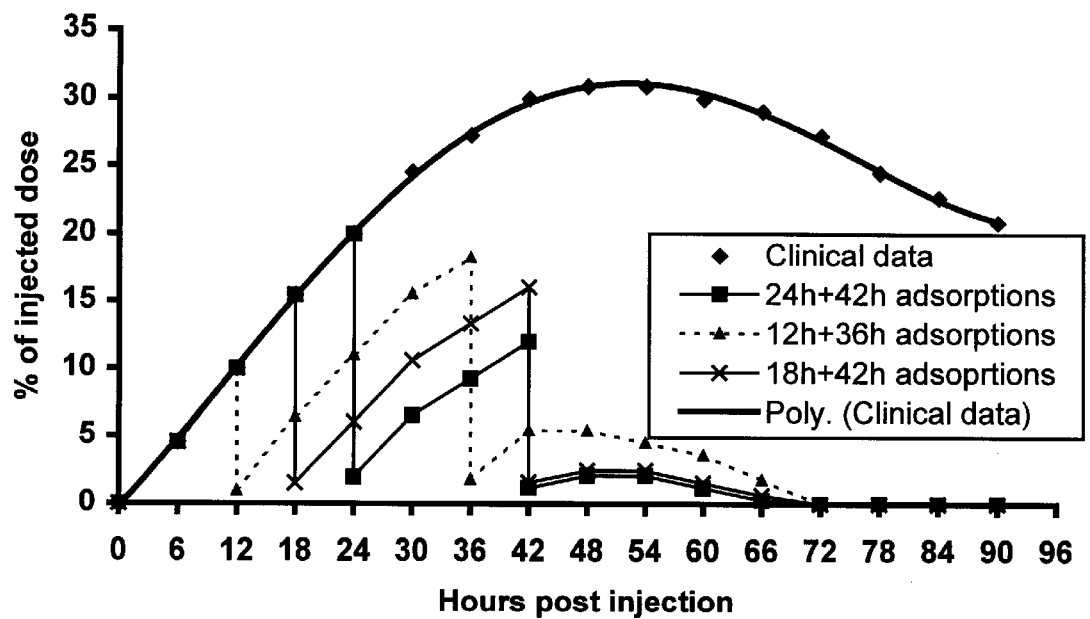
FIG. 1 illustrates a simulation of the effect of Mitradep® treatments on blood levels of a conjugate of $^{90}$Y-HMFG-1 and biotin.

The following preferred embodiments of the invention serve to explain the details of the method in the invention.

As used herein, a "cytotoxic medical agent" includes all cytotoxic agents which, when administered intraperitoneally exert a cell toxic effect, are mainly transported to the blood circulation through the lymphatic route, and can be biotinylated or otherwise labeled with an affinity ligand without severely affecting the efficacy of the drug.

Cytotoxic medical agents commonly used in the treatment of ovarian cancer include cisplatin, carboplatin or taxenes like docetaxel or paclitaxel or analogues or derivatives thereof, bleomycin, anthracyclines and derivatives thereof, alkylating agents like cyclophosphamide, etoposide, anti-estrogen drugs like tamoxifen, GnRH analogues, topoisomerase I inhibitors like Topotecan, naturally occurring toxins like doxorubicin and derivatives thereof.

According to the subject invention, a "targeting agent" is an agent carrying a cytotoxic moiety that, contrary to common cytotoxic medical agents, binds specifically to tumor cell with a high affinity and which could be administered intraperitoneally to a mammal or human being. In a preferred application, the targeting agents are antibodies, which could be of different isotypes and could originate from any species. Of particular interest are the monoclonal antibodies and derivatives thereof. The latter include fragments such as the F(ab')$_2$, F(ab'), F(ab) and the like. They also include genetically engineered hybrids or chemically synthesized peptides based on the specificity of the antigen binding region of one or several target specific monoclonal antibodies e.g. chimeric or humanized antibodies, single chain antibodies etc. Any of these antibodies or fragments or derivative thereof could be modified by the coupling of various number of polyethylene glycol chains in order to optimise the half-life in body fluid and the retention of the antibody or antibody fragments or derivatives, in the tumor tissue. In the most preferred application the antibodies or antibody derivatives should allow for the attachment of a sufficient number of affinity ligands, e.g., biotin residues, to be used for extracorporeal removal through interaction with immobilized receptors, e.g., avidin, without significantly diminishing the binding properties of the targeting agent.

In order to enhance the specificity, tumor specific targeting agents or monoclonal antibodies are used as carriers (immunoconjugates) to carry cytotoxic medical agents (as defined above) and various other "cytotoxic moieties", such as, but not limited to, radionuclides, chemotherapy drugs, synthetic or naturally occurring toxins, immunosuppressive agents, immunostimulating agents and enzymes used in prodrug protocols. The conjugates of targeting agents and cytotoxic medical agents or other cytotoxic moieties are referred to herein as "targeting agent conjugates."

The cytotoxic moiety is preferable a radionuclide such as a gamma-emitter, e.g. iodine-131 or metal ion conjugate, where the metal is selected from a beta-particle emitter, such as yttrium or rhenium. U.S. Pat. No. 4,472,509, Gansow, et al., discloses the use of diethylenetriaminepentaacetic acid (DTPA) chelating agents for the binding of radio metals to monoclonal antibodies. The '509 patent is particularly directed to a purification technique for the removal of non-bonded and adventitiously bonded (non-chelated) metal from radiopharmaceuticals but is illustrative of art recognized protocols for preparation of radioisotopic pharmaceuticals.

According to such general procedures, an antibody specifically reactive with the target tissue associated antigen is reacted with a quantity of a selected bifunctional chelating agent having protein binding and metal binding functionalities to produce a chelator/antibody conjugate. In conjugating the antibodies with the chelators an excess of chelating agent is reacted with the antibodies, the specific ratio being dependent upon the nature of the reagents and the desired number of chelating agents per antibody. It is a requirement that the radionuclides are bound by chelation (for metals) or covalent bonds in such a manner that they do not become separated from the biotinylation/radiolabeling compound under the conditions that the biomolecule conjugates is used (e.g. in patients). Thus, the most stable chelates or covalent bonding arrangements are preferred. Examples of such binding/bonding moieties are: aryl halides and vinyl halides for radionuclides of halogens; $N_2S_2$ and $N_3S$ chelates for Tc and Re radionuclides; amino-carboxy derivatives such as EDTA, DTPA, derivatives Me-DTPA and Cyclohexyl-DTPA, and cyclic amines such as NOTA (1,4,7-triazacyclononane-1,4,7-triacetic acid), DOTA (1,4,7,10-tetraazacyclododecane-N, N', N", N"'-tetraacetic acid), TETA (1,4,8,11-tetraazacyclotetradecane-N, N', N", N"'-tetraacetic acid), CITC-DTPA (-DTPA), SCN-Bz-DOTA (isothiocyanatobenzyl 1,4,7,10-tetraazacyclododecane-N, N', N', N"-tetraacetic acid), and triethylenetetraamine-hexaacetic acid derivatives (Yuangfang and Chuanchu, Pure & Appl. Chem. 63, 427–463, 1991) for In, Y, Pb, Bi, Cu, Sm and Lu radionuclides.

Beta radiation emitters, which are useful as cytotoxic moieties, include isotopes such as scandium-46, scandium-47, scandium-48, copper-67, gallium-72, gallium-73, yttrium-90, ruthenium-97, palladium-100, rhodium-101, palladium-109, samarium-153, rhenium-186, rhenium-188, rhenium-189, gold-198, radium-212 and lead-212. The most useful gamma emitters are iodine-131 and indium-m 114. Other metal ions useful with the invention include alpha radiation emitting materials such as bismuth-212, bismuth-213, and At-211 as well as positron emitters such as gallium-68 and zirconium-89.

In another embodiment of the subject invention, radionuclide-labeled targeting agents are useful not only in treatment of peritoneal cancers, but also for imaging of such cancers.

Thus, according to the subject invention, peritoneal cancer cells can be treated with cytotoxic medical agents (cell-killing drugs) or conjugates of a targeting agent a cytotoxic moiety. Such cytotoxic medical agents and targeting agent conjugates are referred to collectively herein as "biomolecules."

For affinity adsorbents, the matrix may be of various shapes and chemical compositions. It may, for example, constitute a column house filled with particulate polymers, the latter of natural origin or artificially made. The particles may be macroporous or their surface may be grafted, the latter in order to enlarge the surface area. The particles may be spherical or granulated and be based on polysaccharides, ceramic material, glass, silica, plastic, or any combination of these or similar materials. A combination of these could, for example, be solid particles coated with a suitable polymer of natural origin or artificially made. Artificial membranes may also be used. These may be flat sheet membranes made of cellulose, polyamide, polysulfone, polypropylene or other types of material which are sufficiently inert, biocompatible, non-toxic and to which the receptor could be immobilized either directly or after chemical modification of the membrane surface. Capillary membranes like the hollow fibers made from cellulose, polypropylene or other materials suitable for this type of membranes may also be used. A preferred embodiment is a particulate material based on agarose and suitable for extracorporeal applications.

In the preferred embodiment the blood clearance is achieved by the use of a specific adsorption device. Such a device could utilize immobilized anti-species antibodies for the removal of therapeutic antibodies of, e.g., murine origin, or immobilized anti-idiotypic antibodies for removal of therapeutic antibodies regardless of the species origin. In a preferred application an affinity ligand is attached to the biomolecule and the adsorption device contains an immobilized receptor binding specifically to the affinity ligand. Any type of affinity ligand/immobilized receptor combinations can be used in this application, provided that the they do not significantly interfere with the binding affinity and selectively of the biomolecule to the tumor, and provided that the affinity ligand-receptor interaction is not interfered with by blood or other body fluids or tissues being in contact with the biomolecule-affinity ligand conjugate and/or the device receptor. Examples of affinity ligand and receptor combinations include the following: antibodies and antigens or haptens (anti-DNP antibodies and DNP); enzymes and inhibitors (biotin enzymes and avidin or streptavidin inhibitors); and protein and co-factors (intrinsic factor and vitamin $B_{12}$ or cobalamin).

In the most preferred embodiment, the affinity ligand/immobilized receptor combination is biotin or biotin derivatives thereof and biotin binding molecules. In particular, the affinity ligand can be biotin or derivatives thereof and the immobilized receptor can be avidin or streptavidin or any other biotin binding molecule. The affinity ligand pairs of biotin/avidin and biotin/streptavidin are often used in other applications. The very strong interaction (i.e. $K=10^{13}-10^{15}$ $M^{-1}$) of biotin with the proteins avidin and streptavidin (Green, Methods Enzymol. 184, 51–67, 1990; Green, Adv. Prot. Chem. 29, 85–133, 1975) provides a foundation for their use in a large number of applications, both for in vitro and in vivo uses. A further application of the invention is the simultaneous removal of several different biotinylated biomolecules through the same extracorporeal procedure.

As used herein "substantially reducing" the concentration or level of biomolecule or cytotoxic fragment in the blood means a concentration reduction of at least 25%, and in increasing preference, reductions of at least 50%, 60%, 70%, 80%, 90% and 95%.

In summary, the aim of the present invention is to attenuate the patient's toxic exposure. Such toxic exposure can result in haematological side effects, myelosuppression, as well as toxic effects on vital organs through which the toxified blood is passed such as liver, lung, heart, kidney, spleen, etc. The treatment regime can be separated into the following events:

1. Dose calculations dependent on the size of nodules and dissemination of the disease, preferentially based on laparoscopy or CT scan, according to methods known to those skilled in the art.

2. Intraperitoneal infusion of biomolecule or biomolecule-affinity ligand conjugates, e.g., biotinylated immunoconjugate specific for ovarian carcinomas, using methods known to those skilled in the art.

3. Systemic extracorporeal depletion of the biomolecule or biomolecule-affinity ligand conjugate, e.g., biotinylated immunoconjugate, or cytotoxic fragments thereof, from the blood circulation by passing the blood through a receptor (e.g., avidin) coated device on one or several occasions depending on the kinetics of the uptake of the biomolecule-affinity ligand conjugate in the blood circulation and the total dose of the conjugate administered.

The following Examples illustrate the utility and advantages of the subject methods. Example 1 illustrates how extracorporeal treatment can reduce the cytotoxicity associated with intraperitoneal injections of radiolabeled antibody directed to cancerous tissue. Examples 2–5 illustrate the effectiveness of the subject invention in attenuating the patient's toxic exposure. Examples 2–5 illustrate that a radiolabeled anti-ovarian cancer immunoconjugate can be biotinylated to a sufficient degree for extracorporeal depletion without significantly affecting the avidin-binding properties or the biodistribution in the blood and vital organs. Additionally, Example 5 shows that the biotinylated immunoconjugate can be efficiently cleared from the blood circulation.

EXAMPLES

Example 1

Simulation of the Effect of Extracorporeal Adsorption on Blood Levels of Cytotoxic Medical Agent FIG. 1 illustrates the percentage of injected radioactivity in the blood after intraperitoneal administration of $^{90}$Y-HMFG-1 to patients with ovarian cancer as reported by Maraveyas A. et al. (Cancer 73:1067–1075, 1994). These data were utilized to simulate the effects of two extracorporeal adsorptions with Mitradep® (a blood filter having avidin immobilized to agarose particles approved for human use in Sweden) conducted at various or suitable times after administration of the conjugate of antibody and biotin. The following equation, obtained by fourth degree polynomial regression, was utilized for calculations: $y=2*10^{-6}*x^4-0.0004*x^3+0.0104*x^2+0.7863*x-0.1963$ ($R^2=0.9994$).

Each adsorption is assumed to remove 90 per cent of the circulating conjugate. It is also assumed that the rate of transport of conjugate from the intraperitoneal volume to blood or the biological half-life of the conjugate in blood is not influenced by the extracorporeal adsorptions.

When the areas under the curve (AUC) are calculated, the following results were obtained (ECAT is extracorporeal affinity treatment):

| Adsorption 1 Hrs post-inj. | Adsorption 2 Hrs post-inj. | AUC | Reduction (AUC without ECAT)/(AUC with ECAT) |
|---|---|---|---|
| — | — | 2026 | — |
| 12 | 36 | 624 | 3.25 |
| 18 | 42 | 499 | 4.1 |
| 24 | 42 | 417 | 4.85 |

The calculations are under-estimations as data is available up to 90 hours only. The AUC is generally considered as directly correlated to the myelotoxic side effects seen in treatment with the radioimmunoconjugate.

It appears from the foregoing data that the simulated extracorporeal treatment employing adsorptions at 24 and 42 hours could be more effective. Similar analyses conducted in vivo in animal models or in human clinical studies can determine and optimize the number and frequency of adsorption procedures necessary to enhance imaging contrast and/or reduce side effects. Suitable times for extracorporeal treatment depend on the kinetic function (which describes the level of the cytotoxic medical agent in the blood circulation as a function of time after intraperitoneal infusion), the number of extracorporeal (e.g., Mitradep®) treatments, and the optimal time point of treatment(s). The blood kinetic curve is likely to be similar for all types of monoclonal antibodies and the shape is probably the same for smaller targeting molecules as well. Based on the blood kinetic curve, the optimal post-injection extracorporeal treatment time can be calculated by calculating the AUC (without ECAT)/AUC (with ECAT) ratio. The greater this ratio, the less the cytotoxic (radioactive) exposure.

Example 2

Radiolabeling and Biotinylation of HMFG-1-CITC-DTPA

In this and subsequent examples, Indium-111 was used as a substitute for yttrium-90, because the former is a gamma-emitter and possesses less radiation hazard than yttrium-90.

Ten (10) µl of I M Sodium Acetate pH 5.5 was added to a vial containing 22 MBq (40 µl) $^{111}$Indium Chloride to give a final acetate concentration of approximately 0.2 M. 900 µl HMFG-1-CITC-DTPA was added to the $^{111}$In solution. (DTPA is diethylenetriamine pentaacetic acid.) After incubation for 30 minutes in room temperature, 40 µl of 50 mM disodium EDTA (ethylene diamine tetraacetic acid) in acetate buffer was added to quench the reaction. Utilizing gel filtration, the buffer was changed to 0.1 M $NaHCO_3$ pH 8.4.

Four (4) µl of N-hydroxysuccinimide (NHS)-biotin (10 mg/ml DMSO) was added to a vial with 500 µl $^{111}$In-HMFG-1 conjugate (2.25 mg/ml), followed by addition of DMSO to give a final DMSO concentration of 10%. The mixture was incubated for 4 hours at room temperature. Low molecular weight components were removed by gel filtration. The quality of the radio conjugate was determined by TLC and HPLC.

Figure 2:
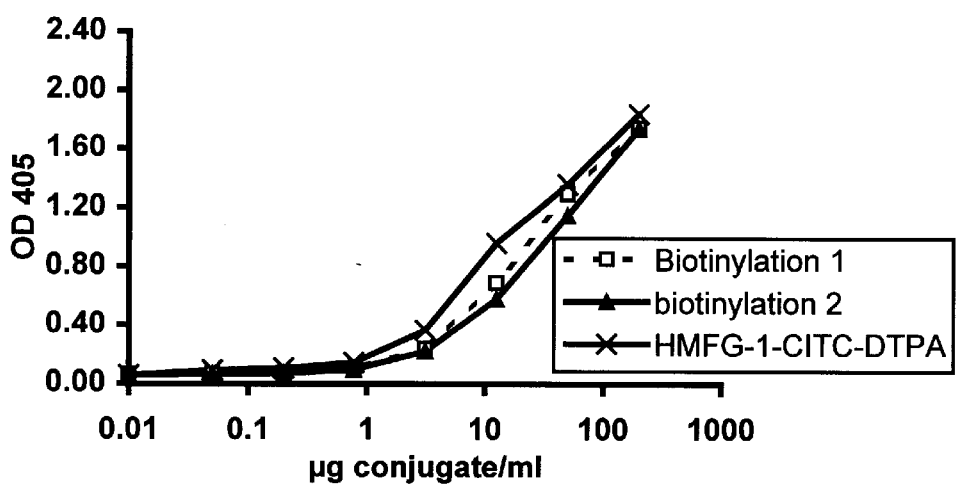
FIG. 2 shows the retention of antigen binding of HMFG-1 antibody labeled with $^{111}$In and biotin on an avidin agarose column.

The antigen-binding reactivity was analyzed after two separate biotinylation procedures conducted on non-radiolabelled HMFG-1-CITC-DTPA. 40 µg of NHS-biotin was added per mg of antibody. As illustrated in FIG. 2, more than 99% of the radioactivity bound to avidin agarose. The binding curves were not significantly different from the curve obtained with HMFG-1-CITC-DTPA.

Example 3

Pharmacokinetics of Conjugates of Biotinylated $^{111}$In-HMFG-1

Figure 3:
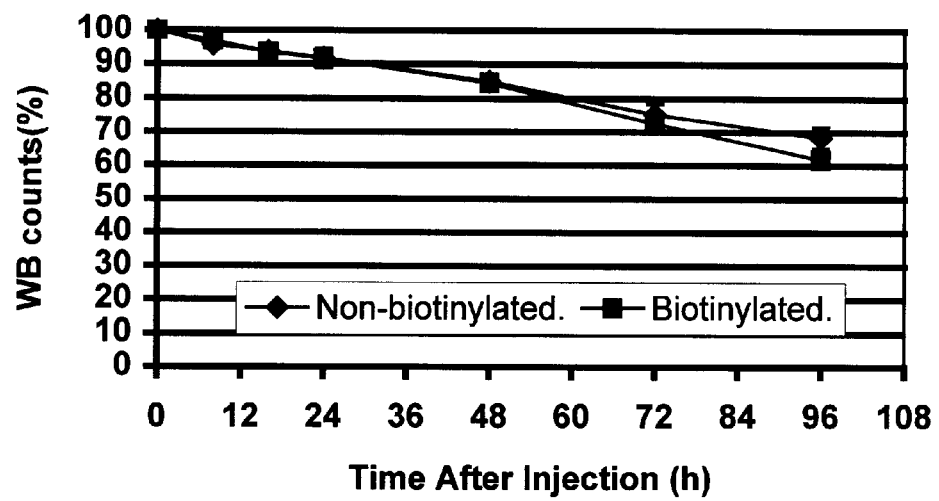
FIG. 3 illustrates the percent reduction in whole body (WB) radioactivity after intraperitoneal injection of $^{111}$In-HMFG-1 in rats.

Rats of the F1 breeding of Brown Norway (BN) and Wistar Furth (WF) rats were injected intraperitoneally with approximately 150 µg of biotinylated HMFG1 labeled with 5 MBq $^{111}$In. Whole body (WB) imaging was performed using a scintillation camera (General Electric 400T, GE, Milwaukee, Wis., USA) equipped with a medium-energy collimator. Images were stored and analyzed with Nuclear MAC 2.7 software. From the images, the total number of counts in the entire body were obtained. After radioactivity decay correction and background subtraction, the counts were used for the calculation of activity retention (%) in the body. See FIG. 3.

Figure 4:
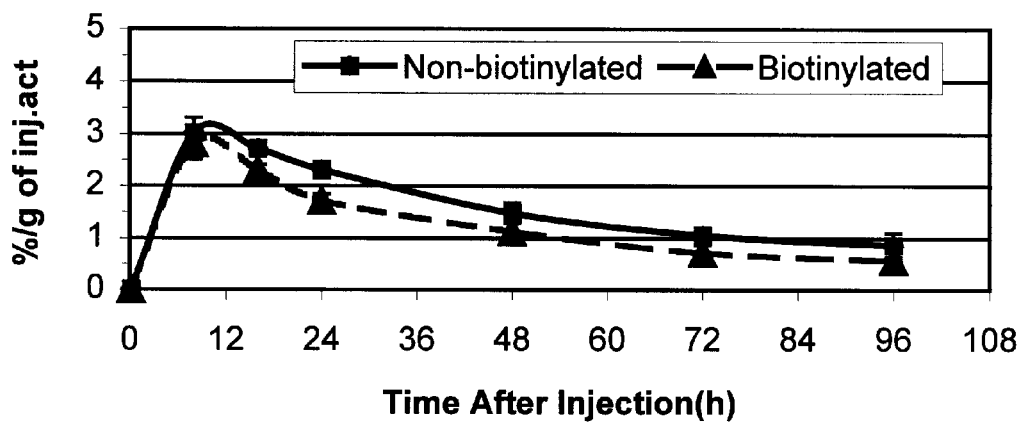
FIG. 4 illustrates the pharmacokinetics of biotinylated $^{111}$In-HMFG-1 following intraperitoneal injection in mice.

To define the pharmacokinetics of biotinylated $^{111}$In-HMFG1, about 0.2 ml blood was obtained from the periorbital venous plexa on the following occasions: 5 min, 8, 16, 24, 48, 72, and 96 hours after injection. The radioactivity was measured in an automatic NaI(T1) scintillation well counter and expressed in percent of injected activity per gram tissue (%/g) corrected for $^{111}$In decay. See FIG. 4.

After peritoneal resorption, a fraction of biotinylated $^{111}$In-HMFG-1 antibody was transferred to the blood circulation reaching maximal activity concentration of 3%/g (about 65% of the injected activity) between 12 h and 16 h post injection.

Example 4

Biodistribution of Conjugates to Organs and Tissues

Figure 5A:
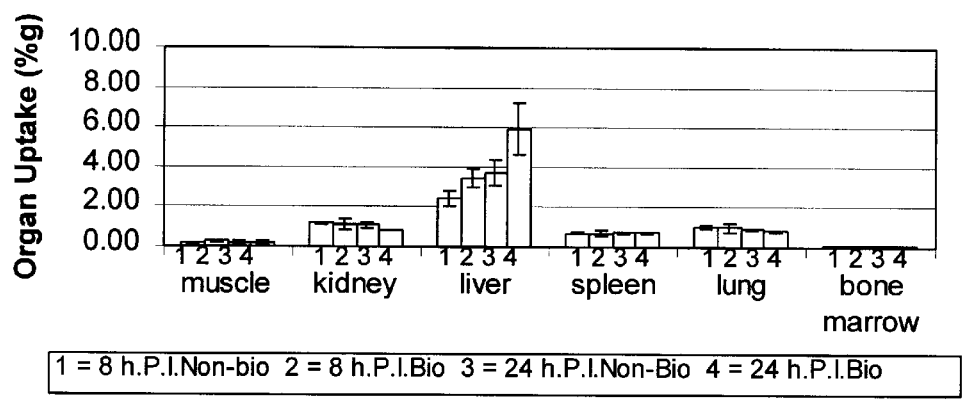
FIGS. 5A and 5B shows the radioactivity uptake in selected rat organs and tissues at selected times following intraperitoneal injection of $^{111}$In-HMFG-1.
Figure 5B:
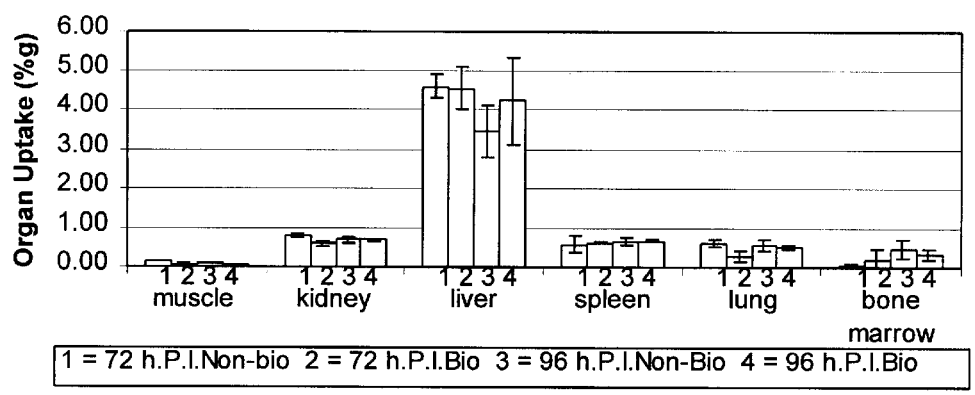
Figure 6:
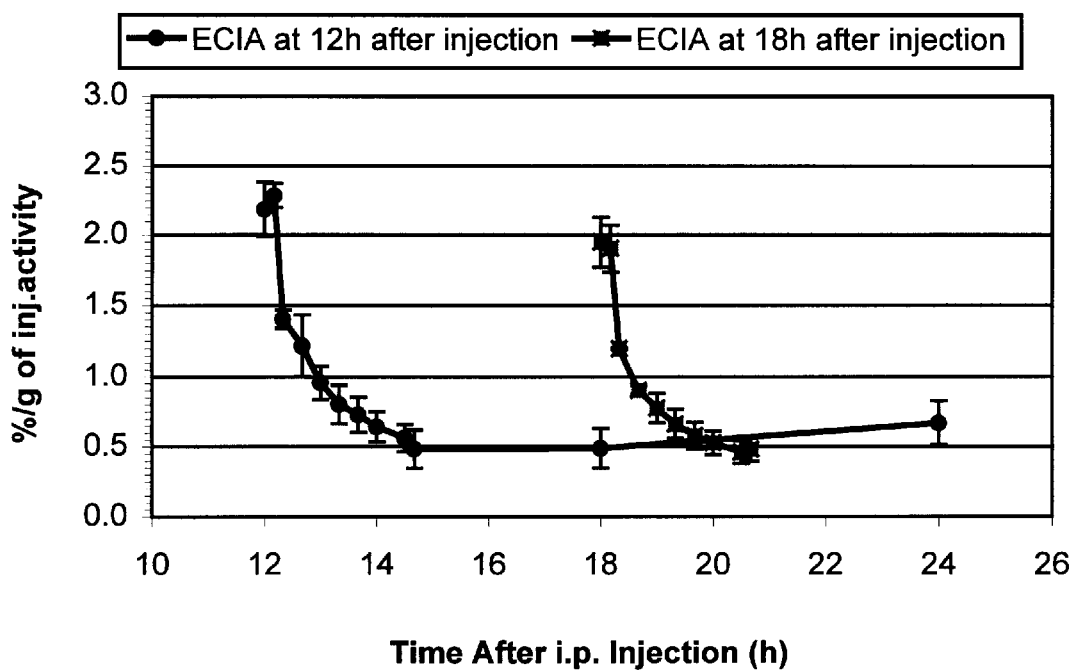
FIG. 6 illustrates the reduction in blood radioactivity following extracorporeal treatment at 12 and 18 hours after intraperitoneal injection (ECIA is extracorporeal immunoadsorption).

Dissections of organs and tissues of interest were performed after 8, 24, 72, and 96 hours. The organs and tissues were removed, weighed, and measured for activity content. The radioactivity was measured in an automatic NaI (T1) scintillation well counter, and the counts were corrected for decay. The distribution of the injected activity is shown in FIGS. 5A and 5B.

Example 5

Extracorporeal Adsorption of Biotinylated $^{111}$In-HMFG-1

The rats underwent arterial and venous catherization for extracorporeal affinity adsorption treatment. Blood was pumped from the arterial catheter through an adsorbent with avidin-agarose at a flow rate of 0.5 ml/min. During a 3-hours treatment approximately 3 blood volumes were processed.

In conclusion, radiolabeled anti-ovarian cancer immunoconjugate as exemplified with $^{111}$In labelled HMFG-1-

CITC-DTPA can be biotinylated to a sufficient degree for extracorporeal depletion without significantly affecting the binding properties or the biodistribution in the blood and vital organs. It has also been shown that the same biotinylated immunoconjugate can efficiently be cleared from the blood circulation.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for improving the treatment of intraperitoneal cancers in mammals comprising:
   a) administering a conjugate intraperitoneally to said mammal, wherein said conjugate comprises an antibody or derivative thereof bound to a single molecule which comprises a biotin or avidin and a radiolabel; and
   b) substantially reducing the level of said conjugate or a cytotoxic fragment thereof in the blood circulation at suitable times intervals, whereby side effects associated with circulating conjugate or cytotoxic fragment are reduced.

2. The method of claim 1, wherein the reduction of conjugate or cytotoxic fragment in the circulation is achieved by passing the blood or a component thereof through an extracorporeal adsorption device.

3. The method of claim 2, wherein the blood component is serum or plasma.

4. The method of claim 2, wherein the extracorporeal device comprises a solid support with a receptor bound thereto, and wherein the biotin or avidin has a high affinity to the receptor.

5. The method of claim 1 wherein the step of substantially reducing the level of the conjugate or cytotoxic fragment thereof in the blood circulation also enhances imaging of the intraperitoneal cancer.

* * * * *